United States Patent [19]
Ando et al.

[11] Patent Number: 5,506,243
[45] Date of Patent: Apr. 9, 1996

[54] SULFONAMIDE DERIVATIVES

[75] Inventors: Ryoichi Ando, Kanagawa; Toshiro Sakaki, Tokyo; Chizuko Takahashi; Yoshiyuki Fujimura, both of Kanagawa, all of Japan

[73] Assignee: Mitsubishi Kasei Corporation, Tokyo, Japan

[21] Appl. No.: 233,963

[22] Filed: Apr. 28, 1994

[30] Foreign Application Priority Data

Apr. 28, 1993 [JP] Japan .................................. 5-102782

[51] Int. Cl.$^6$ .................... A61K 31/44; A61K 31/47; A61K 31/50; A61K 31/505; C07D 213/70

[52] U.S. Cl. .................. 514/345; 514/231.5; 514/238.2; 514/247; 514/249; 514/255; 514/259; 514/262; 514/269; 514/299; 514/308; 514/312; 514/335; 514/345; 514/366; 514/369; 514/372; 514/376; 514/370; 514/381; 514/384; 514/398; 514/407; 514/424; 514/443; 514/445; 514/452; 514/456; 514/460; 514/463; 514/470; 514/473; 514/604; 544/59; 544/106; 544/228; 544/239; 544/253; 544/257; 544/265; 544/298; 544/315; 544/316; 544/319; 544/384; 544/408; 546/138; 546/153; 546/242; 546/243; 546/293; 548/183; 548/213; 548/228; 548/251; 548/263.2; 548/307.1; 548/361.5; 548/470; 548/482; 548/484; 548/486; 549/14; 549/399; 549/416; 549/430; 549/466; 549/474

[58] Field of Search ............................. 546/293; 514/345, 514/604; 564/90

[56] References Cited

U.S. PATENT DOCUMENTS 5,081,284  1/1992  Higuchi ................................ 560/159

FOREIGN PATENT DOCUMENTS 0504938  9/1992  European Pat. Off. .
504938  9/1992  European Pat. Off. .
2490632  3/1982  France .

OTHER PUBLICATIONS

Sasaki et al., J. Enzyme Inhibition, 1990, vol. 3, No. 3, pp. 195–201.

Mehdi S. Cell–penetrating inhibitors of Calpain TIBS 16 Apr. 1991 pp. 150–153.

*Primary Examiner*—C. Warren Ivy
*Assistant Examiner*—Evelyn Huang
*Attorney, Agent, or Firm*—Wenderoth, Lind & Ponack

[57] ABSTRACT

Since sulfonamide derivatives of the present invention show strong inhibitory activity against cysteine protease such as calpain papain, cathepsin B, cathepsin H, cathepsin L, they can be used as remedies for muscular dystrophy, cataract, myocardial infarction, stroke, Alzheimer's disease, amyotrophia, osteoporosis, hypercalcemia or the like.

11 Claims, No Drawings

SULFONAMIDE DERIVATIVES

BACKGROUND OF THE INVENTION

1. Field of the Invention

The present invention relates to a novel sulfonamide derivative. More particularly, it relates to a novel sulfonamide derivative or a salt thereof which shows a strong inhibitory activity against cysteine protease such as calpain, cathepsin B, cathepsin H, cathepsin L, and papain.

2. Description of the Related Art

As the in vivo action of cysteine protease, which papain, calpain, cathepsin and the like belong to, has been elucidated, its abnormal accentuation has been found to cause various diseases. Accordingly, cysteine protease inhibitors have been used as remedies for such diseases. For example, calpain inhibitors have been reported to be effective in an animal model suffering from muscular dystrophy, cataract, myocardial infarction, stroke, while cathepsin inhibitors have been reported to be effective for metastasis of cancer, amyotrophia, osteoporosis, hypercalcemia and the like.

As cysteine protease inhibitors, peptidyl aldehyde derivatives are well known. For example, Leupeptin [Journal of Antibiotics, 22, 183 (1969)], Strepin P-1 [Agricultural and Biological Chemistry, 49, 799 (1985)], Staccopins P1, P2 [Agricultural and Biological Chemistry, 51, 861 (1987)] and the like have been isolated from a microbial culture medium. In addition, various compounds have been synthesized. For example, MDL 28170 [Biochemical and Biophysical Research Communications, 157, 1,117 (1988)] and Calpeptin [Journal of Enzyme Inhibition, 3, 195 (1990)] are well known. Under the present conditions, most of the N-termini of these peptidyl aldehyde derivatives are free amino acid or amide derivative thereof or carbamate thereof, and few have been reported about N-terminal in the form of sulfonamide [Japanese Patent Application Laid-open No. 268145-1990; Journal of Antibiotics, 41, 220 (1988); Journal of Biochemistry, 98, 975 (1985); Developmental Biology, 105, 246 (1984); Journal of Pharmacobio-Dynamics, 6, 643 (1983); Japanese Patent Application Laid-open No. 054157-1982; Proceedings of National Academy of Science of the U.S.A., 76, 1,131 (1979); Japanese Patent Application Laid-open No. 137951-1975]. Compounds having stronger cysteine protease inhibitory activity have been sought.

SUMMARY OF THE INVENTION

The present inventors have conducted research to identify compounds having strong cysteine protease inhibitory activity, and have attained the present invention.

That is, the present invention is directed to sulfonamide derivatives of the following general formula (I):

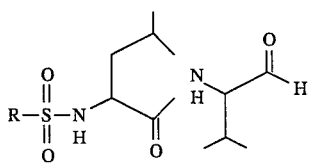

(I)

(wherein R is $C_{6-14}$ aryl or a heterocyclic residue each of which may have substituents or the salt thereof.

DETAILED DESCRIPTION OF THE INVENTION

The present invention will be illustrated in detail.

The present compound is a sulfonamide derivative or a salt thereof represented by the following general formula (I):

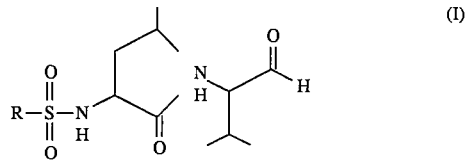

(I)

wherein R is $C_{6-14}$ aryl (phenyl, naphthyl, anthryl, etc.) which may have one or more substituents (substituents are selected from a group consisting of a halogen atom such as a fluorine atom, a chlorine atom, a bromine atom; $C_{1-5}$ alkyl such as methyl, ethyl, propyl, iso-propyl, butyl, iso-butyl, sec-butyl, tert-butyl, pentyl, isopentyl, neopentyl; trifluoromethyl; $C_{1-5}$ alkoxy such as methoxy, ethoxy, propoxy, iso-propoxy, butoxy, iso-butoxy, tert-butoxy, pentyloxy, isopentyloxy; $C_{1-5}$ cyclic acetal residue such as methylenedioxy, ethylenedioxy, propylenedioxy, butylenedioxy; hydroxyl; $C_{2-6}$ acyloxy such as acetoxy, propionyloxy, butyryloxy, valeryloxy; formyl; carboxyl; $C_{2-6}$ alkoxycarbonyl such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl; oxo; $C_{2-6}$ acyl such as acetyl, propionyl, butyryl, valeryl; amino; $C_{1-5}$ monoalkylamino such as methylamino, ethylamino, propylamino, isopropylamino, butylamino, isobutylamino, tert-butylamino, pentylamino, iso-pentylamino; $C_{2-10}$ dialkylamino such as dimethylamino, ethylmethylamino, diethylamino, methylpropylamino, diisopropylamino; $C_{2-6}$ acylamino such as acetylamino, propionylamino, isopropionylamino, butyrylamino, iso-butyrylamino, valerylamino; carbamoyl; and $C_{2-6}$ alkylcarbamoyl such as methylcarbamoyl, ethylcarbamoyl, propylcarbamoyl, isopropylcarbamoyl, butylcarbamoyl, tert-butylcarbamoyl, pentylcarbamoyl (hereinafter referred to as 'Group 1')) or a heterocyclic residue (a heterocyclic residue having 1 to 4 hetero atoms selected from a group consisting of oxygen, sulfur and nitrogen and having, in total, 5 to 10 carbon atoms constituting a ring, for example, furyl, pyranyl, benzofuranyl, iso-benzofuranyl, chromenyl, chromanyl, isochromanyl, thiophenyl, benzothiophenyl, pyrrolyl, pyrrolinyl, pyrrolidinyl, imidazolyl, imidazolinyl, imidazolydinyl, pyrazolyl, pyrazolinyl, pyrazolidinyl, triazolyl, tetrazolyl, pyridyl, 1-oxopyridyl, piperidinyl, pyrazinyl, piperazinyl, pyrimidinyl, pyridazinyl, indolizinyl, indolyl, indolinyl, iso-indolyl, isoindolinyl, indazolyl, benzimidazolyl, purinyl, quinolizinyl, quionolyl, iso-quinolyl, phthalazinyl, naphthyridinyl, quinoxalinyl, quinazolinyl, cinnolinyl, pteridinyl, oxazolyl, oxazolidinyl, isoxazolyl, isoxazolidinyl, thiazolyl, thiazolidinyl, isothiazolyl, isothiazolidinyl, dioxolanyl, dioxanyl, dithianyl, morpholinyl, thiomorpholinyl, which may have one or more substituents (substituents are selected from 'Group 1').

The preferred example of the compound of the present invention includes those wherein R is phenyl, 2-fluorophenyl, 3-fluorophenyl, 4-fluorophenyl, 2-chlorophenyl, 3-chlorophenyl, 4-chlorophenyl, 2,6-dichlorophenyl, 2,4,6-trichlorophenyl, 2-methylphenyl, 3-methylphenyl, 4-methylphenyl, 3,5-dimethylphenyl, 4-tertbutylphenyl, 4-trifluoromethylphenyl, 2-methoxyphenyl, 3-methoxyphenyl, 4-methoxyphenyl, 3,4-dimethoxyphenyl, 2-hydroxyphenyl, 3-hydroxyphenyl, 4-hydroxyphenyl, 4-acetoxyphenyl, 2-carboxyphenyl, 3-carboxyphenyl, 4-carboxyphenyl, 2-methoxycarbonylphenyl, 3-methoxycarbonylphenyl, 4-methoxycarbonylphenyl, 2-acetylphenyl, 3-acetylphenyl, 4-acetylphenyl, 2-dimethylaminophenyl, 3-dimethylaminophenyl, 4-dimethylaminophenyl, 1-naphthyl, 2-naphthyl, 4-chloro-1-naphthyl, 6-chloro-1-naphthyl, 3-chloro-2-naphthyl, 8-chloro-2-naphthyl, 4-dimethylamino-1-naphthyl, 8-dimethylamino-2-naphthyl, 2-pyridyl, 3-pyridyl, 4-pyridyl, 3-chloro-2-pyridyl, 2-chloro-3-pyridyl, 3-methyl-2-pyridyl, 2-methyl-3-pyridyl, 1-furyl, 2-furyl, 5-chloro-1-furyl, 1-thienyl, 2-thienyl, 4-quinolyl, 1-isoquinolyl, 5-isoquinolyl or 1-methyl-5-isoquinolyl.

Particularly preferred example includes the compounds in which R is a phenyl or a pyridyl group.

The sulfonamide derivative of the present invention represented by the above general formula (I) is converted into a pharmaceutically acceptable salt thereof. Particular embodiment of such salts includes a metal salt such as lithium, sodium, potassium, magnesium, calcium salt or ammonium salt such as ammonium, methylammonium, dimethylammonium, trimethylammonium, dicyclohexylammonium salt which may be formed in the presence of an acid group; and mineral acid salt such as hydrochloride, hydrobromide, sulfate, nitrate, phosphate or an organic acid salt such as methanesulfonate, benzenesulfonate, paratoluenesulfonate, acetate, propionate, tartrate, fumarate, maleate, malate, oxalate, succinate, citrate, benzoate, mandelate, cinnamate, lactate which may be formed in the presence of a basic group.

As the configuration of the asymmetric carbon of the sulfonamide derivative represented by the above general formula (I), the compound may independently occur as R-, S- or RS-configuration. The process for production of the present compound will now be explained. The present sulfonamide derivatives can be produced, for example, by the following process:

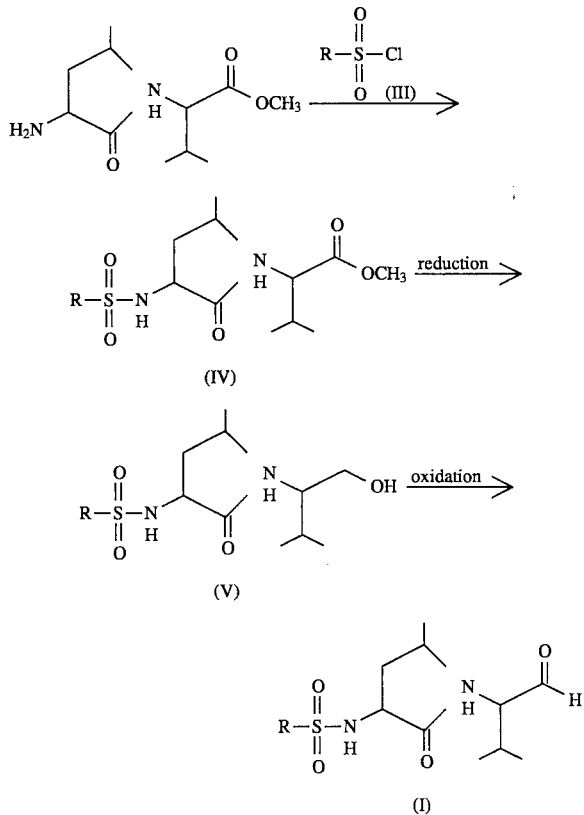

(in the above general formula (I), R is as defined above).

Leucylvaline methyl ester represented by the above formula (II) is dissolved in a solvent such as tetrahydrofuran, ethyl acetate, dimethylformamide, dichloromethane, chloroform, 1,2-dichloroethane, and sulfonyl chloride of the above general formula (III) is added thereto in the presence of a base such as pyridine, triethylamine to afford a compound of the above general formula (IV). The ester of the compound (IV) is reduced with a reducing agent such as lithium aluminum hydride, lithium borohydride, sodium borohydride to give an alcohol (v), which is oxidized to aldehyde using an oxidizing agent such as sulfur trioxide/pyridine, oxalyl chloride/dimethyl sulfoxide, chromic acid/pyridine, potassium dichromate, manganese dioxide to give a sulfonamide derivative of the above general formula (I).

when the compound of the present invention is clinically employed, the ratio of the therapeutically active ingredient to the carrier may vary within the range of 1 to 90% (by weight). For example, the present compound may be orally administered in the form of granule, powder, tablet, hard capsule, soft capsule, syrup, emulsion, suspension or other liquid for internal use. Alternatively, it may be administered as an injection by intravenous, intramuscular or subcutaneous administration. It may also be administered as a suppository. It may be formulated as powder for injection and prepared before use. Pharmaceutical organic or inorganic solid or liquid carrier or diluent suitable for oral, intestinal, parenteral administration may be used for preparation of the present medicine. Excipient used for production of solid preparation includes, for example, lactose, sucrose, starch, talc, cellulose, dextrin, kaolin, calcium carbonate. Liquid preparation for oral administration, that is, emulsion, syrup, suspension or other liquid for internal use may contain water or vegetable oil as a conventional inert diluent. Such preparation may also contain additives other than inert diluent, such as wetting agent, suspending aid, sweetener, flavor, colorant or preservative. It may be formulated as liquid preparation and filled in a capsule constituting of absorbable substance such as gelatin. Solvent or suspending agent used for production of parenteral preparation, i.e., injection, suppository or the like includes, for example, water, propylene glycol, polyethylene glycol, benzyl alcohol, ethyl oleate, lecithine and the like. A base used for suppository includes, for example, cacao butter, emulsified cacao butter, laurin tallow, witepsol and the like. The preparation may be compounded according to the conventional method.

The clinical dose of the present compound is generally 0.01–1,000 mg/day for an adult by oral administration. However, such dose may be preferably changed depending on age, pathema, symptom as needed. The present medicine of the above daily dosage may be administered once a day, or twice or three times a day with proper intervals. Alternatively, it may be intermittently administered.

When the present compound is used as an injection, a dose of 0.01–100 mg is desirably administered continuously or intermittently for an adult.

DESCRIPTION OF THE PREFERRED EMBODIMENTS

The present invention will be illustrated in detail in the following syntheses and examples. The present invention is not construed to be limited by these syntheses and examples so long as they are within the scope of the present invention.

Synthesis 1

Production of N-Phenylsulfonyl-L-leucyl-L-valine methyl ester

L-Leucyl-L-valine methyl ester hydrochloride (16.8 g) was dissolved in methylene chloride (500 ml), to which were added benzensulfonyl chloride (10.6 g) and triethylamine (16.7 ml). The resulting mixture was stirred at room temperature for 4 hours, then diluted hydrochloric acid was added. The solution was extracted with methylene chloride. The extract was sequentially washed with water, saturated aqueous sodium bicarbonate, saturated saline, and dried over magnesium sulfate and filtered. The filtrate was concentrated and purified by silica gel column chromatography (eluent: hexane: ethyl acetate=2:1) to give 16.3 g of the objective compound as a crystal.

Yield; 71%

NMR (CDCl$_3$, δ): 0.74 (d, J=6.9 Hz, 3H), 0.78 (d, J=6.4 Hz, 3H), 0.80 (d, J=6.9 Hz, 3H), 0.87 (d, J=6.6 Hz, 3H), 1.47 (m, 2H), 1.68 (m, 1H), 1.99 (m, 1H), 3.73 (s, 3H), 3.76 (m, 1H), 4.35 (dd, J=8.6 Hz, 4.8 Hz, 1H), 5.29 (d, J=8.4 Hz, 1H), 6.27 (d, J=8.2 Hz, 1H), 7.46–7.57 (m, 3H), 7.87 (ddd, J=5.9 Hz, 1.4 Hz, 1.4 Hz, 2H)

Synthesis 2

Production of N-phenylsulfoyl-L-leucyl-L-valinol

N-Phenylsulfonyl-L-leucyl-L-valine methyl ester obtained in Synthesis 1 (660 mg) was dissolved in tetrahydrofuran (15 ml) and sodium borohydride (163 rag) was added thereto. Subsequently, the reaction solution was heated to 55° C., to which was added dropwise methanol (2.5 ml) over 12 minutes. The resulting mixture was further stirred at 55° C. for an hour. After the reaction solution was allowed to cool to room temperature, diluted hydrochloric acid was added. Half of the solution was distilled off under reduced pressure. The concentrate was extracted with methylene chloride. The extract was washed with saturated saline, dried over magnesium sulfate and filtered. The filtrate was concentrated and the resulting residue was reacted twice in the same manner as described above, then recrystallized from diethyl ether to give 373 mg of the product.

Yield; 61%

NMR (CDCl$_3$, δ): 0.52 (d, J=6.3 Hz, 3H), 0.80 (d, J=6.2 Hz, 3H), 0.86 (d, J=6.8 Hz, 3H), 0.93 (d, J=6.8 Hz, 3H), 1.48 (m, 2H), 1.60 (m, 1H), 1.81 (m, 1H), 3.56–3.72 (m, 4H), 5.12 (d, J=5.5 Hz, 1H), 6.44 (d, J=8.8 Hz, 1H), 7.51–7.63 (m, 3H), 7.89 (ddd, J=6.1 Hz, 1.2 Hz, 1.2 Hz, 2H)

EXAMPLE 1

Production of N-phenylsulfonyl-L-leucyl-L-valinal

Oxalyl chloride (53 μl) was dissolved in methylene chloride (4 ml) and cooled to −78 ° C., then dimethyl sulfoxide (90 μl) was added thereto. The reaction solution was stirred at −78° C. for 15 minutes, then N-phenylsulfonyl-L-leucyl-L-valinol obtained in Synthesis 2 (176 mg) dissolved in methylene chloride (4 ml) and dimethyl sulfoxide (140 μl) was added dropwise. After 15 minutes, triethylamine (545 μl) was added to the reaction solution and warmed to room temperature. After stirring at room temperature for an hour, diluted hydrochloric acid was added to the reaction solution and extracted with methylene chloride. The extract was sequentially washed with water and saturated saline, then dried over magnesium sulfate and filtered. The filtrate was concentrated and purified by silica gel column chromatography (eluent: hexane: ethyl acetate=2:1) to give 139 mg of the product (amorphous solid).

Yield; 80%

IR: (KBr, cm$^{-1}$): 1,734, 1,655

NMR (CDCl$_3$, δ): 0.76 (d, J=6.4 Hz, 3H), 0.84 (d, J=7.2 Hz, 3H), 0.87 (d, J=6.6 Hz, 3H), 0.89 (d, J=6.8 Hz, 3H), 1.51 (m, 2H), 1.63 (m, 1H), 2.17 (m, 1H), 3.78 (ddd, J=8.4 Hz, 8.4 Hz, 5.3 Hz, 1H), 4.38 (dd, J=7.7 Hz, 4.4 Hz, 1H), 5.36 (d, J=8.1 Hz, 1H), 6.44 (d, J=7.3 Hz, 1H), 7.50– 7.58 (m, 3H), 7.88 (dd, J=7.9 Hz, 1.2 Hz, 2H), 9.58 (s, 1H)

EXAMPLE 2

Production of N-3-pyridylsulfonyl-L-leucyl-L-valinal

The title compound was prepared in the same manner as Syntheses 1 and 2 and Example 1.

Melting Point: 43°–46° C.

IR: (KBr, cm$^{-1}$): 1,734, 1,664

NMR (CDCl$_3$, δ): 0.77 (d, J=6.4 Hz, 3H), 0.84 (d, J=6.3 Hz, 3H), 0.89 (d, J=6.9 Hz, 3H), 0.90 (d, J=6.6 Hz, 3H), 1.52 (dd, J=6.9 Hz, 6.9 Hz, 2H), 1.72 (m, 1H), 2.16 (m, 1H), 3.88 (dd, J=15.7 Hz, 7.6 Hz, 1H), 4.40 (dd, J=7.8 Hz, 4.6 Hz, 1H), 5.73 (d, J=8.9 Hz, 1H), 6.39 (d, J=8.2 Hz, 1H), 7.46 (dd, J=8.1 Hz, 4.9 Hz, 1H), 8.17 (d, J=8.1 Hz, 1H), 8.79 (d, J=4.0 Hz, 1H), 9.08 (br.s, 1H), 9.59 (s, 1H)

Experiment

Measurement of calpain inhibitory activity m-Calpin was purified from brains of rats according to the method described in a document (Journal of Biological Chemistry, 259, 3,210 (1984)), and its inhibitory activity was measured according to the method described in a document (Journal of Biological Chemistry, 259, 12,489 (1984)). The results are shown in Table 1. For comparison, inhibitory activity of leupeptin (N-terminus is in the form of amide) and calpeptin (N-terminus is in the form of carbamate) was also measured. Table 1 shows that the present compound strongly inhibits cysteine protease such as calpain.

TABLE 1

| Compound | IC$_{50}$ (μM) |
| --- | --- |
| Example 1 | 0.011 |
| Example 2 | 0.0065 |
| Leupeptin | 0.36 |
| Calpeptin | 0.046 |

What is claimed is:

1. A sulfonamide derivative having the following general formula (I):

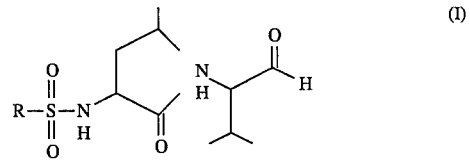

wherein R is C$_{6-14}$ aryl which has no substituent or a heterocyclic residue which may have one or more substituents or the salt thereof.

2. A compound of claim 1, wherein the said substituent is selected from the group consisting of halogen atoms, C$_{1-5}$ alkyl, trifluoromethyl, C$_{1-5}$ alkoxy, C$_{1-5}$ cyclic acetal, hydroxyl, C$_{2-6}$ acyloxy, formyl, carboxyl, C$_{2-6}$ alkoxycarbonyl, oxo, C$_{2-6}$ acyl, amino, C$_{1-5}$ monoalkylamino, C$_{2-10}$ dialkylamino, C$_{2-6}$ acylamino, carbamoyl and C$_{2-6}$ alkylcarbamoyl.

3. A compound of claim 1, wherein the substituent which the heterocyclic group may have is selected from a group consisting of halogen atoms and $C_{1-5}$ alkyl.

4. A compound of claim 1, wherein the heterocyclic residue has 1 to 4 hetero atoms selected from the group consisting of oxygen, sulfur and nitrogen, and total number of carbon atoms constituting the ring is 5 to 10.

5. A compound of claim 1, wherein the heterocyclic residue is furyl, pyranyl, benzofuranyl, isobenzofuranyl, chromenyl, chromanyl, isochromanyl, thiophenyl, benzothiophenyl, pyrrolyl, pyrrolinyl, pyrrolidinyl, imidazolyl, imidazolinyl, imidazolydinyl, pyrazolyl, pyrazolinyl, pyrazolidinyl, triazolyl, tetrazolyl, pyridyl, 1-oxopyridyl, piperidinyl, pyrazinyl, piperazinyl, pyrimidinyl, pyridazinyl, indolizinyl, indolyl, indolinyl, isoindolyl, isoindolinyl, indazolyl, benzimidazolyl, purinyl, quinolizinyl, quionolyl, isoquinolyl, phthalazinyl, naphthyridinyl, quinoxalinyl, quinazolinyl, cinnolinyl, pteridinyl, oxazolyl, oxazolidinyl, isoxazolyl, isoxazolidinyl, thiazolyl, thiazolidinyl, isothiazolyl, isothiazolidinyl, dioxolanyl, dioxanyl, dithianyl, morpholinyl or thiomorpholinyl.

6. A compound of claim 5, wherein the heterocyclic residue is furyl, pyridyl, thiophenyl, quinolyl or isoquinolyl.

7. A compound of claim 1, wherein R is phenyl.

8. A compound of claim 1, wherein R is pyridyl.

9. A pharmaceutical composition which comprises the compound of any one of claims 1–2 or 4–9 and a pharmaceutically acceptable carrier.

10. A pharmaceutical composition of claim 9 for treatment of a disease caused by abnormal accentuation of cysteine protease.

11. A pharmaceutical composition of claim 10, wherein the disease caused by abnormal accentuation of cysteine protease is muscular dystrophy, cataract, myocardial infarction, stroke, Alzheimer's disease, amyotrophia, osteoporosis or hypercalcemia.

\* \* \* \* \*